(12) United States Patent
Gupta

(10) Patent No.: US 7,569,558 B2
(45) Date of Patent: Aug. 4, 2009

(54) TOPICAL DELIVERY OF TRACE METALS FOR SKIN CARE

(75) Inventor: Shyam K Gupta, Scottsdale, AZ (US)

(73) Assignee: Bioderm Research, Scottsdale, AZ (US)

(*) Notice: Subject to any disclaimer, the term of this patent is extended or adjusted under 35 U.S.C. 154(b) by 486 days.

(21) Appl. No.: 11/308,290

(22) Filed: Mar. 15, 2006

(65) Prior Publication Data

US 2006/0183708 A1 Aug. 17, 2006

Related U.S. Application Data

(63) Continuation-in-part of application No. 10/306,948, filed on Nov. 29, 2002, now abandoned.

(51) Int. Cl.
*A61K 8/02* (2006.01)
*A61K 31/665* (2006.01)
*A61K 31/315* (2006.01)
*A61K 31/31* (2006.01)
*A61K 31/30* (2006.01)
*A61K 31/28* (2006.01)

(52) U.S. Cl. .................. 514/100; 514/494; 514/497; 514/499; 514/505; 424/401

(58) Field of Classification Search .............. 514/100, 514/494, 497, 499, 505; 424/401
See application file for complete search history.

(56) References Cited

FOREIGN PATENT DOCUMENTS

EP 1298069 A2 * 9/2002
GB 2044265 * 10/1980

OTHER PUBLICATIONS

Harris (Cellular copper transport and metabolism, annual review of nutrition, 2000, vol. 20 pp. 291-310).*

* cited by examiner

*Primary Examiner*—Johann R Richter
*Assistant Examiner*—Luke E Karpinski

(57) ABSTRACT

The present invention relates to a method for topical delivery of trace metals for the modulation of certain metalloenzymes. The method of topical delivery of the present invention comprises; (i) mixing of a trace metal salt of a phosphorylated nitrogen heterocyclic base complexed with a chelating agent [Figure 1], and (ii) a carrier, and (iii) topical application of said mixture. The modulation of metalloenzymes such as Superoxide Dismutase, Elastase, Tyrosinase, Matrix metalloproteases, and Ubiquitin-Proteasome pathway by the methods of the present invention is useful for providing anti-inflammatory, skin whitening, wrinkles reduction, skin aging control, cellular antioxidant, acne control, hair growth modulation, and skin damage control benefits.

9 Claims, No Drawings

TOPICAL DELIVERY OF TRACE METALS FOR SKIN CARE

This is a continuation-in-part of U.S. patent application Ser. No. 10/306,948 filed Nov. 29, 2002 now abandoned (US Patent Application Pre-grant Publication 20040105894) that relates to trace metal derivatives of certain nucleotides and glycosides.

The present invention relates to a method for topical delivery of trace metals for the modulation of certain metalloenzymes. The said method comprises; (i) mixing of a trace metal salt of a phosphorylated heterocyclic base complexed with a chelating agent [FIG. 1], and (ii) a carrier, and (iii) topical application of said mixture. The modulation of metalloenzymes such as Superoxide Dismutase, Elastase, Tyrosinase, Matrix metalloproteases, and Ubiquitin-Proteasome pathway by the method of the present invention is useful for providing anti-inflammatory, skin whitening, wrinkles reduction, skin aging control, cellular antioxidant, acne control, hair growth modulation, and skin damage control benefits.

[FIG 1]. Chemical Structures of Trace Metal Salts of Phosphorylated Heterocyclic Bases Complexed with a Chelating Agent.

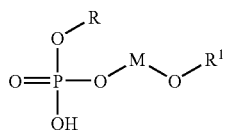

Wherein,
M is selected from Cu, Zn, Mn, Co, Cr, V=O, and Ni; and
R is selected from,

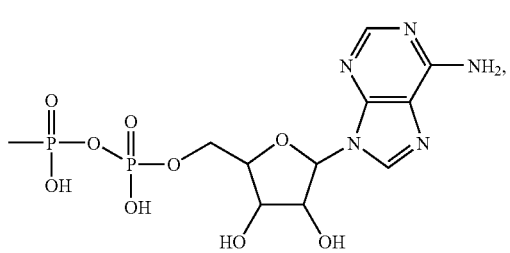

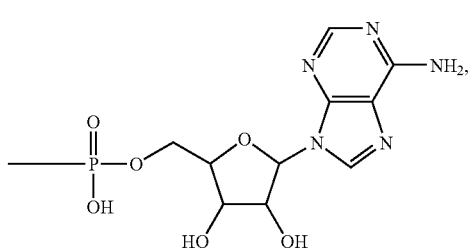

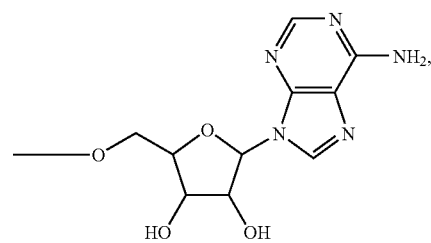

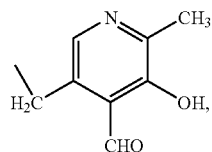

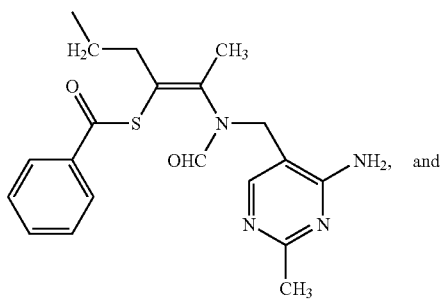

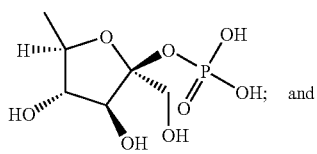

and $R^1$ is selected from,

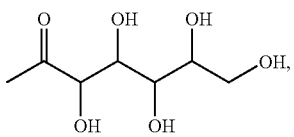

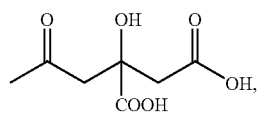

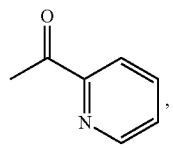

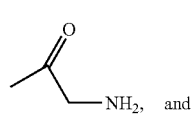

and

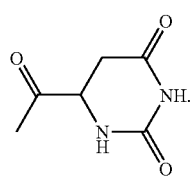

The specific examples of compounds of formula (I) are;
Copper adenosine triphosphate gluconate of formula (II);

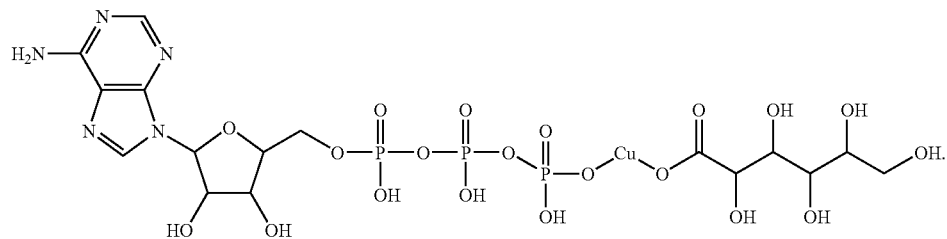

Chromium benfotiamine picolinate of formula (III); and

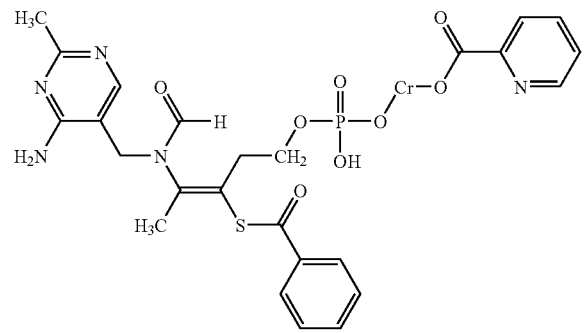

Vanadium pyridoxal-5-phosphate oxo glycinate of formula (IV);

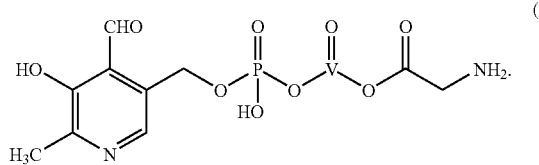

Maintaining a youthful appearance is of great importance to many people, particularly in an aging population. Several of the visible signs of aging result from its effects on the skin. The passage of time is reflected in the appearance of wrinkles and fine lines; by a slackening of tissue; a loss of cutaneous elasticity; a leathery or dry appearance; by the yellowing of the skin which becomes duller and loses its radiance; and the appearance of age-spots that are especially visible in face, neck, chest, and arms.

About 30 elements are recognized as essential to life. Some are required in macroscopic amounts in essentially all forms of life: H, Na, K, Mg, Ca, C, N, O, P, S, and Cl. The others occur in trace or ultratrace quantities. Fe, Cu, and Zn are at the top end of this "trace" scale. The other elements required are Li, B, F, Si, V, Cr, Mn, Co, Ni, As, Se, Mo, W, and I. The trace and ultratrace metals most important for human cellular functions are Fe, Cu, Zn, Mn, Co, Cr, V, and Se. In human body there are about 4 to 6 grams of iron, 2 to 3 grams of zinc, and only 250 mg of copper. Cobalt is found in Vitamin B12. There is one cobalt atom in this vitamin; the latter is present in only 2 to 5 mg quantity in the human body.

Many of these elements, especially trace metals, are bound at the active-site of biologically important metalloenzymes. The examples of such metalloenzymes that are of interest for their topical modulation are included in Table 1.

TABLE 1

Biologically Important Metalloenzymes

| Metalloenzyme | Function | Metal |
|---|---|---|
| Tyrosinase | Tyrosine oxidation | Cu, Zn |
| Superoxide Dismutase | Superoxide detoxification | Cu, Zn, Mn |
| Catalase | Peroxide decomposition | Fe |
| Matrix Metalloproteases | Protein hydrolysis | Zn |
| Dopamine Hydroxylase | Dopamine conversion | Cu |
| Amine Oxidase | Elastin, collagen synthesis | Cu |
| Cytochrome c Oxidase | Oxidation | Cu |
| Ceruplasmin | Oxidation | Cu |
| Glutathione Peroxidase | Peroxide detoxification | Se |
| Glucose Tolerance Factor | Glucose metabolism | Cr |

Brief descriptions of the biochemistry of some of the important trace metals and their role in metalloenzymes-mediated systems are presented below.

Selenium is now recognized as an important trace element for human body. It is present in glutathione peroxidase. Glutathione peroxidase belongs to the family of selenoproteins and plays an important role in the defense mechanisms of mammals against oxidative damage by catalyzing the reduction of a variety of hydroperoxides, using glutathione as the reducing substrate. Four distinct species of glutathione peroxidase have been identified in mammals to date, the classical cellular enzyme, and the phospholipid hydroperoxide metabolizing enzyme, the gastrointestinal tract enzyme and the extracellular plasma enzyme.

Chromium is important for glucose tolerance in human body. Chromium is a constituent ingredient of what is called the Glucose Tolerance Factor. It works closely with insulin to facilitate the uptake of glucose into cells. In individuals with impaired glucose tolerance, such as those with diabetes, hypoglycemia, and obesity, supplementation with chromium is of paramount importance. Without chromium, blood sugar levels stay elevated because the action of insulin is blocked so that glucose is not transported into the cells. Unlike iron, zinc, copper, molybdenum, and selenium, chromium has not been found in a metalloprotein with biologic activity. Therefore, the apparent biologic activity of chromium in promoting glucose tolerance remains unexplained. The estimated requirement for chromium in humans is about 1 mcg/day, but only 1 to 3% of trivalent chromium is absorbed. In the USA, chromium intakes range from 20 to 50 mcg/day, with plasma levels from 0.05 to 0.50 mcg/L. The Food and Nutrition Board of the NAS/NRC states that a safe, adequate intake of chromium for an adult is 50-200 mcg/day.

U.S. patent application Ser. No. 20060029642 (Miljkovic et al.) disclose certain metal-containing complex matrices, and especially chromium-containing matrices that are produced from a water-soluble preparation that is derived from an item suitable for human consumption. In particularly contemplated aspects, the water soluble preparation is an extract or filtrate of disintegrated brewer's yeast, and the so prepared complex mixture is combined with a chromium (3+) ions source.

U.S. patent application Ser. No. 20060024383 (Berlin) discloses an ingestible composition that contains policosanol and chromium and/or chromium salts, and which may be used for treating, preventing and or reducing metabolic syndrome, hypercholesterolemia and hypoglycemia related diseases, total cholesterol, LDL-cholesterol, LDL/HDL ratio, triglycerides, coronary heart disease (heart attacks and strokes), inflammation, deep-vein thrombosis, immunoregulatory diseases, cardiovascular diseases, obesity, insulin resistance, dyslipidemia, raised blood pressure, fatigue, premenstrual syndrome, anxiety, depression and/or neurodegenerative disorders, and/or raising HDL cholesterol and/or lean body mass in humans and animals. The method comprises administering policosanol and chromium and/or chromium salts which together effectively lower both blood glucose and LDL/HDL cholesterol ratio. Typically, the administered composition includes about 0.1-10:1 parts by weight of policosanol to chromium and/or chromium salts.

Nickel is an essential nutrient for higher animals. Although a number of cellular effects of nickel have been documented, a deficiency disease has not been described in man. Nickel is found in highest concentrations in lung, kidney and some hormone-producing tissues. Although nickel-specific enzymes have yet to be identified in higher animals, nickel can activate or inhibit a number of enzymes that usually contain other elements. The production or action of some hormones (prolactin, adrenaline, noradrenalin, and aldosterone) responds to changes in nickel concentration. Within cells, nickel alters membrane properties and influences oxidation/reduction systems. Nickel has great affinity for cellular structures such as chromosomes and ion channels, but its influence on them at normal tissue concentrations is not known. Recently, describing the active sites of six nickel metalloenzymes highlights different functions of nickel in catalysis: methyl-coenyzme M reductase, urease, hydrogenase, superoxide dismutase, carbon monoxide dehydrogenase and acetyl-coenzyme A synthase [Ermler et al., Curr Opin Struc Biol (6): 749 (1998)].

One of the major roles played by trace elements in human biochemistry is in metalloenzymes. This term is applied to enzymes that not only require the participation of a metal ion at the active site to function but bind that metal ion or ions strongly even in the resting stage (F. A. Cotton and G. Wilkinson, Advanced Inorganic Chemistry, Fifth Edition, John Wiley, 1988). Known metalloenzymes now number several hundred. The role of the metal atoms in enzymatic catalysis is currently an active area of research. The metal ion in metalloenzymes is held in an enforced stereochemistry, called "entatic state", which enhances its capacity to bind and activate the substrate.

Metalloenzymes may be considered as a subclass of the metalloproteins. Metalloproteins are proteins that incorporate one or more metal atoms as a normal part of their structure. This includes not only metalloenzymes but also respiratory proteins like hemoglobin and myoglobin, electron transport proteins such as cytochromes and ferredoxins, and metal storage proteins.

In many cases it is possible to remove the metal atoms and then restore them or replace them by others without collapse of the overall protein structure. The protein from which the metal ions have been removed is called the apoprotein, the use of this term usually implying that the active metalloprotein can be recovered on restoration of the metal ions.

Most of prior art methods to treat aged skin have been based on purely organic compounds. The role of bioinorganic and bio-organic metal molecules in the treatment of skin disorders related to the biological processes of aging is now being understood in greater detail, and recognized by the scientific community. In recent years it has become clear that transition metal such as Cu, Zn, Mn, Cr, Co, and Se are essential for normal development and function of human cells. Copper is the third most abundant trace element in human body, with vitamin-like impact on living systems. Copper functions as a cofactor in over 30 enzymes. The ability of copper to cycle between oxidized $Cu^{2+}$ and a reduced $Cu^+$ state is used by cuproenzymes involved in redox reactions, the two most important examples being Cu/Zn superoxide dismutase and cytochrome C oxidase. Cu/Zn Superoxide dismutase (SOD) is an important enzyme responsible for the destruction of toxic superoxide anion in human body that directly relates to the processes of skin aging and inflammation. The enhancement or increment of SOD functions for antiaging and anticancer benefits is of current scientific and consumer interest. Some of these aspects have recently been disclosed by several authors in recently published text books, such as Valentine et al. [(Advances in Protein Chemistry, vol. 60, pp. 93-121, Academic Press, CA (2002)]; and Massaro [(Handbook of Copper Pharmacology and Toxicology, Humana Press, NJ (2002)], which are quoted here only for reference. It has also become clear that ATP, a major nucleotide present in human body, plays a major role in copper transport, in the form of copper transporting ATPase enzyme, that utilizes the energy of ATP-hydrolysis to transport copper from the cytosol through various cell membranes [Tsivkovskii et al. (J. Biol. Chem., 277, 976-983 (2002); Nakayama et al. (Oncology Reports, 8, 1285-1287 (2001); Wunderli-Ye et al. (Biochem. Biophys. Res. Commun., 280, 713-719 (2001)]. These disclosures point to possible importance of nucleotide complexes of copper in the bioavailability and intra-cellular transport of copper in humans. Despite the obviousness of this, the methods for the topical application or penetration of such nucleotide complexes of trace metals remain unknown in the prior art. Wijnhoven, et al. (U.S. Pat. No. 6,277,605) disclose an interesting role of divalent metals, such as copper, zinc, and manganese, in the complexation with DNA molecules that results in the bond distance increase of nucleic acid components, resulting in the annealing of the DNA helix. A simple oxidation-reduction step of such divalent metal ions can cause annealing or reannealing of such separated DNA strands. This indicates a prospective application of copper zinc, and manganese complexes of nucleic acids, nucleosides, and nucleotides in cosmetic and biomedical control of the process of skin aging. The methods for the topical delivery or penetration of such essential trace metals by such complexes, despite their obvious need, have been unknown in the prior art.

Copper is one of the most important trace elements. Copper exists in several biologically important oxidation states. It is of further importance to review this, since such various forms of copper can have significantly different biological or cosmetic functions or involve specialized methods for their topical deposition and their further penetration to cytosol. Copper biomolecules can occur in four types of copper centers. These four copper types, and their characterization methodologies, are identified in FIG. 2.

[FIG. 2]. Types of Copper Sites in Metalloenzymes.

| COPPER TYPE | MAIN CHARACTERISTICS |
|---|---|
| Copper (I) | Colorless, diamagnetic, epr silent |
| Normal Copper (II) | Visible and epr spectra typical of tetragonally Coordinated $Cu^{2+}$ |
| Blue Copper (II) | The epr shows abnormally small $A_{11}$; very intense absorption ($\epsilon$ about 5000) at 600 nm. |
| Coupled $(Cu^{II})_2$ | Abnormal visible spectrum; Diamagnetic and epr silent. |

While many copper biomolecules contain copper in only one form, for example "blue" or "normal", there are also numerous cases where several different types of copper are present and that can provide difficulties in working out their mode of action, or even their applications. From the data in Figure 2, it is clear that the identification of specific copper species, when several different types of such species may be present, is not an easy task. Yet such species may have different biological roles. It is thus important to develop copper biomolecules that are distinct in their chemical state and biological function for any topical application.

The "normal" copper (II) sites are those in which Cu2+ ion is coordinated by a square set of ligands, usually all nitrogen atoms, such as those present in imidazole moiety of one (or several) histidine molecules. There may be additional ligands occupying more distant coordination sites above and below that square plane of nitrogen ligands. Such copper (II) sites are easily identified by spectral analysis of such copper complexes. The active site of bovine Superoxide Dismutase enzyme, one of the best-known examples of "normal" copper (II) site is illustrated in FIG. 3; all bond distances are in Angstrom units. It is to be noted that this active site also contains zinc as a cofactor. It is to be noted that copper in such "normal" copper (II) sites is electronically bound to four different nitrogen atoms.

[FIG 3]. Active Site of Superoxide Dismutase.

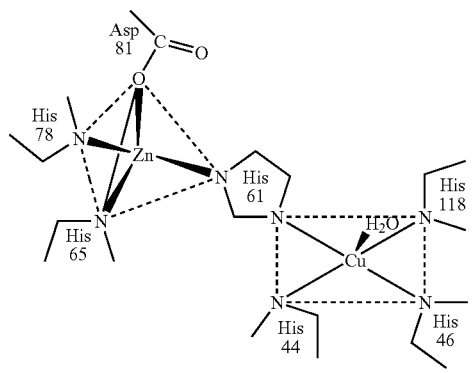

The "blue" copper (II) state entails environment quite unlike those in "normal" copper (II) tetragonal complexes. Numerous sophisticated spectroscopic analyses have been made of both the biomolecules themselves and their model systems. However, only X-ray crystallographic data are most reliable. It is to be noted that copper in "blue" copper (II) sites is electronically bound to four different atoms, two of which are nitrogen and two of which are sulfur atoms [FIG. 4].

[FIG. 4]. "Blue Copper" Active Site of Plastocyanin.

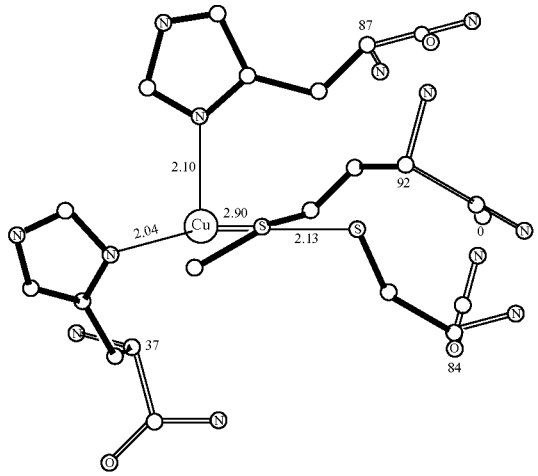

Coupled (Cu II)2 is found most commonly in respiratory proteins of phyla Mollusca and Anthropoda, for example squid, octopus, lobster, and crabs. These proteins, called hemocyanins, are very large that contains subunits. Each subunit contains a pair of Cu atoms, and those atoms can bind one molecule of oxygen per pair of copper atoms. The two-copper active site of hemocyanins is also found in enzyme tyrosinase. In humans this enzyme converts phenols to catechols that leads to the eventual formation of skin pigment, melanin. It is to be noted that copper in "coupled" (Cu II)2 is electronically bound to a minimum of four different atoms, two of which are nitrogen and two of which can be oxygen.

From the discussion above and the inspection of FIGS. 2 to 4, the following points are clear so far; (i) Copper in copper metalloenzymes can be found in several distinctly different chemical states, each of which has a specific function; (ii) Copper in excessive amounts in a cell, present in a free state, can cause cellular toxicity; (iii) Copper generally requires four coordination sites in metalloenzymes, all four of which can be nitrogen, or two of which can be nitrogen and the other two can be sulfur or oxygen atoms from appropriate donor ligands; (iv) Superoxide dismutase also requires zinc and manganese as cofactors; (vi) It is clear to see that copper (II) can also bind with sulfur ligands, in addition to nitrogen atoms; and (viii) From the example of tyrosinase enzyme, it is known that copper (II) can also bind with oxygen ligands, in addition to nitrogen atoms.

Of over 30 enzymes that require copper in their active site, superoxide dismutase is most important from the viewpoint of skin aging and inflammation. Superoxide dismutase (SOD) is one of the enzymes that are most directly linked to superoxide anion detoxification, and, as its production slows down, the process of aging accelerates. Among other biologically important cuproenzymes, the formation of elastin and collagen is a function of amine oxidase, which is another example of a copper-containing metalloenzyme. The skin pigmentation, or melanin formation, is a function of tyrosinase, which is a copper-based monooxygenase class of metalloenzyme. Ceruloplasmin, a copper-containing metalloenzyme, has a role in the iron transport in human body. Dopamine hydroxylase, another copper-based metalloenzyme, is present in adrenal glands, and it converts dopamine to norepinephrine. SOD occurs in three distinct forms in mammalian systems; (i) SOD containing copper and zinc (CuZnSOD, SOD1), which is usually located in the cytosol; (ii) SOD containing manganese (MnSOD, SOD2), which is usually located in mitochondria (MnSOD); and (iii) Another SOD containing Cu and Zn (CuZnSOD, SOD3), which is found in extra-cellular spaces. Additionally, many bacterial SOD contain iron.

In mammalian systems, CuZnSOD (SOD1) catalyses the dismutation of the superoxide anion radical (O2-.), as shown in [FIG. 5].

[FIG. 5]. Dismutation of Superoxide Anion Radical by SOD.

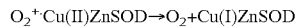

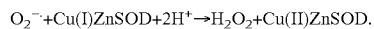

One product of this reaction, H2O2, is also a harmful substance. Hydrogen peroxide is detoxified by catalase, a heme iron metalloenzyme.

The superoxide anion (O2-.) exhibits numerous physiological toxic effects including endothelial cell damage, increased microvascular permeability, formation of chemotactic factors such as leukotrienes, recruitment of neurophils at the sites of inflammation, lipid peroxidation, and oxidation, release of cytokines, DNA single-strand damage, and formation of peroxynitrite anion (ONO2-.), a potent cytotoxic and pro-inflammatory molecule.

Excess superoxide anion can also lead to the formation of highly oxidizing species such as hydroxide and peroxide radicals. Superoxide radical anion, and the peroxynitrite anion formed in its reaction with NO, cause cell death from ischemic tissue. Most of these physiological effects lead to skin aging and tissue degeneration [(Macarthur et al., Proc. Natl. Acad. Sci. USA, 97, 9753-9758 (2000)]. In this capacity, SOD acts as an antioxidant inhibiting aging and carcinogenesis.

Preventing tissue and cell damage caused by reactive oxygen species in mammals has received wide scientific interest, as stated by Hellstrand et al. (U.S. Pat. No. 6,462,067). Free radicals such as superoxide ions, hydroxy radicals, and oxides are known as a major factor of degeneration and thus the ageing of the skin. They destruct the proteins and lipids of the cellular membrane, affect the DNA and also decompose the hyaluronic acid, a key substance of the skin. Under normal biological conditions there is an equilibrium ratio between the free radicals coming up and their embankment by endogenous chemical or enzymatic systems. Additional outside stress factors such as aggressive atmosphere, tobacco smoke, ultraviolet radiation etc. may overload these inherent immune systems and shift the equilibrium in favor of the free radicals. Inflammation or ageing phenomena of the skin may occur, indicating a need for compensation by cosmetic products. Among principal enzymes that have an effect on aging process, catalase, glutathione peroxidase, ascorbate peroxidase, and superoxide dismutase are most important. The enhancement of superoxide dismutase as a method to control various human ailments including aging has been studied extensively, for example Dugas et al. (U.S. Pat. No. 6,426,068), Anggard et al. (U.S. Pat. No. 6,455,542), Hellstrand et al (U.S. Pat. Nos. 6,462,067; 6,407,133), Golz-Berner et al. (U.S. Pat. No. 6,426,080), and others. Medical researchers have attempted to design low-molecular weight SOD mimics (synzymes) that would mimic the natural SOD enzyme in removing superoxide radical anion, [O2-.], and the perhydroxyl radical, [HO2.], as well as preventing formation of peroxynitrite anion, [ONO2-.].

It is well recognized that metalloenzymes and protein-based metal complexes are too large in their molecular weight to be useful for any topical applications where high bioavailability is desired. Such molecules have thus found applications in areas such as wound healing where their presence on skin surface is more beneficial, and their absorption into deeper layers of skin is not desired. It is for this reason that such molecules have not found applications in areas that require their enhanced bioavailability into deeper layers of skin, for example anti-aging, collagen synthesis enhancement, and skin whitening. Superoxide dismutase itself has been used in topical applications for antiaging compositions. However, the molecular weight of this enzyme is so large that its penetration into deeper layers of skin is highly unlikely. Any perceived benefits are most likely the inadvertent result of the separation of copper from the enzyme itself and its subsequent absorption into the skin. This separation of copper from superoxide dismutase in topical preparations can result from various chelating agents that are also used in such compositions.

In order to circumvent the difficulties encountered in the bioavailability of metalloenzymes and protein-based metal complexes from topical applications, including complexes that contain copper or zinc, smaller molecular weight models that mimic the active site of larger molecular weight metalloenzymes have been extensively studied and reported by, for example, Pickart et al. (U.S. Pat. Nos. 5,858,993; 5,888,522; 5,698,184; 5,550,183; 5,554,375; 5,164,367; 4,665,054; 4,760,051; 4,810,693 and 4,877,770; U.S. patent application Ser. No. 20050276766); Pallenberg et al., (U.S. Pat. Nos. 6,017,880 and 5,538,945); and Lawyer et al., (U.S. Pat. No. 6,042,848). Other biomimetic superoxide dismutase models include complexes in which copper has been replaced with an isosteric manganese atom. The preparation of these biomimetic models is very difficult, and many such compositions are not suitable for topical applications. Moreover, it is to be noted that despite the therapeutic promise of the above-mentioned metal complexes, toxicity and tissue irritation occur with many metal complexes. For example, while copper-salicylate complexes and numerous copper-salicylate analogs possess anti-inflammatory activities, other salicylate analogs such as the copper (II) complex of salicylaldehyde benzoyl hydrazone are highly toxic to tissues. Similarly, copper(II)-Gly-L-His-L-Lys supports cellular viability and possesses anti-inflammatory and healing actions, yet close synthetic aroylhydrazone analogs of its copper-binding region are extremely toxic to cells and tissues.

Another problem with copper complexes for topical therapeutic use concerns the binding affinity of copper ion to the complexing molecule. While a defined copper-complex can be synthesized, its topical use places it in the physiological milieu of the tissues where a plethora of literally hundreds of compounds compete for binding to the copper ion, which can form electrostatic bonds to as many as six separate molecules. If the copper is removed from the complex and becomes loosely bound, then tissue irritation occurs. Further complications arise when such metal complexes are formulated into carrier creams or ointments. Various chemicals are added to the formulations to increase adherence to skin and wound surfaces and to enhance the penetration of the complexes into the target tissue. Yet, since many of these substances, for example chelating agents, also bind to the metals, the expected therapeutic benefits may be nullified or significantly attenuated.

A yet another problem exists for the development of topical penetration systems for copper and other trace metals. It is well known that trace metals such as copper, iron, and nickel can catalyze extensive oxidation of fatty organic ingredients that are commonly present in topical preparations in the presence of air. Such oxidation results in the product discoloration and malodor formation. Additionally, any skin beneficial ingredients that are present in such formulations can also decompose or transform into non-functional materials from such oxidation. It is thus very common to use chelating agents such as EDTA in topical compositions to bind with copper and iron in order to prevent such oxidation. The use of such chelating agents is also known to deactivate a number of prior art low molecular weight copper transporting ingredients such as copper peptides and copper amino acids. It would thus be highly desirable to develop low molecular weight copper transporting ingredients for topical applications that are not deactivated by the chelating agents, and that do not cause the oxidation of other ingredients in such topical compositions.

While transport proteins can perform the transport of copper from digestive system, the transport of copper and other trace metals from skin surface via topical delivery systems with transport proteins is not practical, as such large molecular weight copper carrier proteins cannot absorb and penetrate through the upper layers of skin. Smaller molecular weight transporter molecules must thus be devised for topical systems to transport trace metals from the upper layers of skin into the deeper layers of skin. Similarly, the delivery of chaperone proteins [Roat-Malone, Bioinorganic Chemistry, A Short Course, Wiley-Interscience, NJ, 2002] from topical preparations is at present not technologically feasible because of their very large molecular weight.

From the above discussion it is clear that certain trace metals are very important for human biology. The delivery systems for several trace metals are already known, most of which are based on ingestion. It is also clear that trace metals such as copper and chromium must be delivered in their correct oxidation or coordination state to the enzyme site. It is also known (Pickart et al.) that the presence of any chelating agents can be harmful for the topical delivery of trace metals. Pickart et al. also teach that despite the therapeutic promise of the above-mentioned metal complexes, toxicity and tissue irritation occur with many metal complexes [(see, e.g., Johnson et al., Inorg. Chem. Acta, 67: 159-165 (1982); Pickart et al., Biochem. Pharm., 32: 3868-3871 (1983); and Pickart et al., Lymphokines 8: 425-446 (1983)].

The present invention circumvents the difficulties of topical penetration of trace metals. The trace metals such as copper, zinc, iron, and manganese that are necessary for the proper functioning of SOD and other metalloenzymes can be transfused to the active-site of such metalloenzymes by methods of their topical application of the present invention.

The present invention discloses a simple method of topical application for penetration of trace metals that comprises; (i) mixing of a trace metal phosphorylated nitrogen heterocyclic base complexed with a chelating agent, with (ii) a carrier, and (iii) the topical application of said mixture to a suitable dermal surface.

The phosphorylated nitrogen heterocyclic base is represented by general structural features, [Nitrogen Heterocyclic Base-Alkyl-Phosphate], as further illustrated in [FIG. 6], or [Nitrogen heterocyclic Base-Mono Saccharide-Phosphate], as further illustrated in [FIG. 7]. The key examples of phosphorylated nitrogen heterocyclic base include nucleotides such as Adenosine Monophosphate, Adenosine Diphosphate, Adenosine Triphosphate, and phosphorylated derivatives of Vitamin B1 and Vitamin B6, such as Benfotiamine, Thiamine Phosphate, Allithiamines, and Pyridoxal-5-phosphate.

[FIG. 6]. Structure of Benfotiamine, Representing General Features of [Nitrogen Heterocyclic Base-Alkyl-Phosphate] Structure.

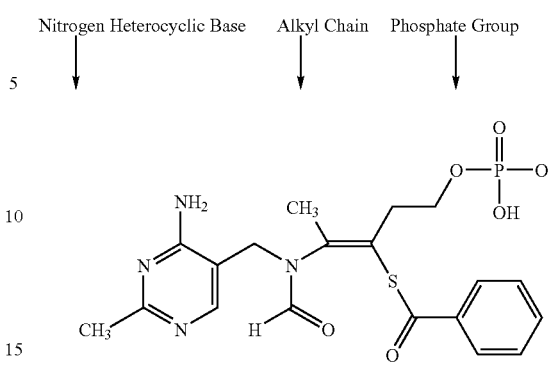

[FIG. 7]. Representing General Features of [Nitrogen Heterocyclic Base-Monosaccharide-Phosphate] Structure.

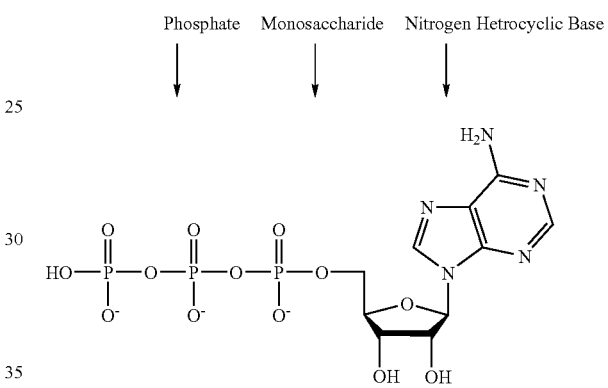

The trace metal phosphorylated nitrogen heterocyclic base complexed with a chelating agent is represented by general structural features, [Phosphorylated Nitrogen Heterocyclic Base-Trace Metal-Chelating Agent] Complex, as further illustrated in [FIG. 8]. The examples include copper, zinc, manganese, cobalt, chromium, vanadium, or nickel salts of Adenosine Monophosphate, Adenosine Diphosphate, Adenosine Triphosphate, Benfotiamine, Thiamine Phosphate, thiamine pyrophosphate, pyridoxamine-5-phosphate, prosultiamine, or Pyridoxal-5-phosphate complexed with gluconic acid, citric acid, picolinic acid, EDTA, orotic acid, phytic acid, 8-hydroxyquinoline, and metal salt of said chelating agents, and combinations thereof.

[FIG. 8]. ATP-Cu-Gluconate Complex. An Example of [(Phosphorylated Nitrogen Heterocyclic Base)-(Trace Metal)-(Chelating Agent)] Complex.

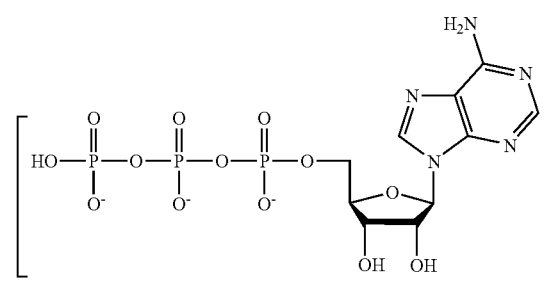

-continued
Phosphorylated Nitrogen Heterocyclic Base

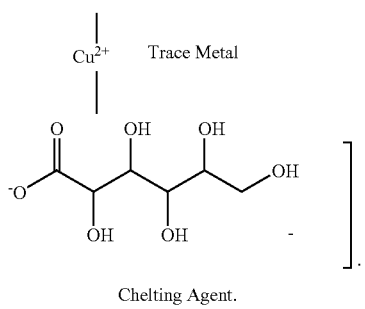

Chelting Agent.

The examples of trace metal include copper, zinc, manganese, cobalt, chromium, vanadium, selenium, nickel, and combinations thereof.

The examples of chelating agent include various chelating agents well known in the prior art that includes gluconic acid, citric acid, picolinic acid, EDTA, orotic acid, phytic acid, 8-hydroxyquinoline, amino acid, peptide, and metal salts of said chelating agents, and combinations thereof.

The examples of trace metal salt of phosphorylated nitrogen heterocyclic base complexed with a chelating agent include Copper Adenosine Triphosphate Gluconate, Chromium Benfotiamine Picolinate, and Vanadium Pyridoxal-5-phosphate Oxo Glycinate.

The amount of trace metal salt of a phosphorylated nitrogen heterocyclic base complexed with a chelating agent can be from about 0.0001% to about 50% by weight, although the minimum and maximum amounts can be determined by the amount of topical penetration desired and the solubility of said complex in a solvent or carrier.

The examples of peptide include glutathione, Carnosine, and like. It is preferred to include peptides that contain an amino acid moiety such as cysteine, histidine, and serine that can form a chelate with the trace metal. Glutathione, for example, contains cysteine and carnosine contains histidine moieties.

The carrier is selected from a lotion, cream, gel, aerosol, serum, mask, fluid, solution, emulsion, suspension, anhydrous fluid, anhydrous paste, or anhydrous gel.

The present invention also discloses a process for a trace metal salt of a phosphorylated nitrogen heterocyclic base complexed with a chelating agent, and comprises; (i) the contact of a chelated trace metal with a phosphorylated nitrogen heterocyclic base or an alkali metal salt of a phosphorylated nitrogen heterocyclic base, and (ii) a solvent, whereby chelated trace metal binds with phosphorylated nitrogen heterocyclic base or its alkali metal salt, and chelated trace metal phosphorylated nitrogen heterocyclic base complex is formed in situ. Alternatively, a different mixing order can be followed, which comprises; (i) the contact of a chelating agent with a trace metal salt of a phosphorylated nitrogen heterocyclic base, and (ii) a solvent, whereby trace metal phosphorylated nitrogen heterocyclic base binds with chelating agent, and chelated trace metal phosphorylated nitrogen heterocyclic base complex is formed in situ.

For example, copper gluconate, which is a trace metal chelate, and Disodium adenosine triphosphate, which is a phosphorylated nitrogen heterocyclic base alkali metal salt, are combined in water, which is a solvent, for 30 minutes at 25 to 30 C. Adenosine triphosphate-Cu-Gluconate complex is formed in situ [Equation 1]. Sodium Gluconate that is also formed from this chemical complexation reaction is available for additional complexation to provide chemical stability.

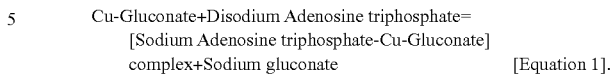

The proposed chemical structure of [Adenosine triphosphate-Cu-Gluconate] complex is shown below:

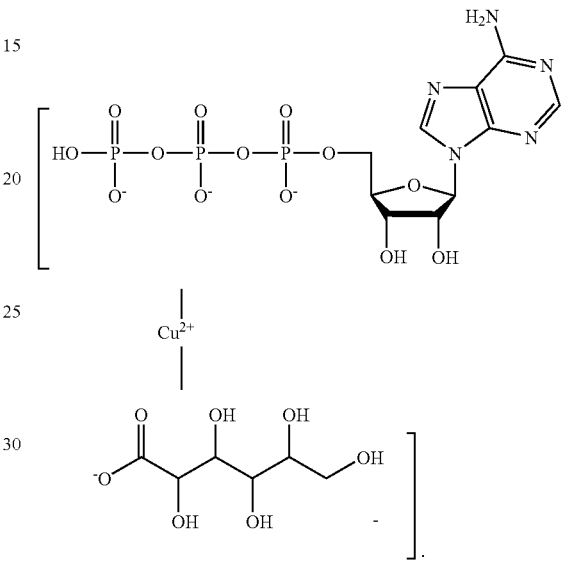

Copper gluconate, which is a trace metal chelate, and Benfotiamine, which is a phosphorylated nitrogen heterocyclic base, are combined in water, which is a solvent, for 30 minutes at 25 to 30 C. Benfotiamine-Cu-Gluconate complex is formed in situ [Equation 2]. Gluconic acid that is also formed from this chemical complexation reaction is available for additional complexation to provide chemical stability.

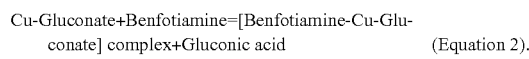

The proposed chemical structure of [Benfotiamine-Cu-Gluconate] complex is shown in [FIG. 9].

[FIG. 9]. Benfotiamine Copper Gluconate.

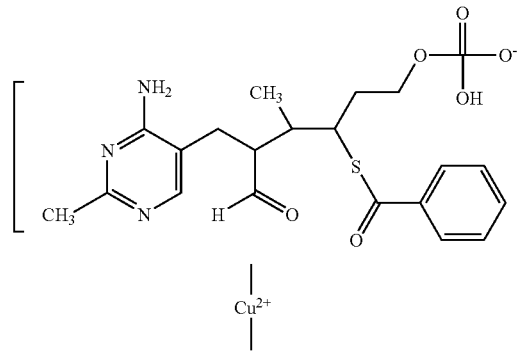

-continued

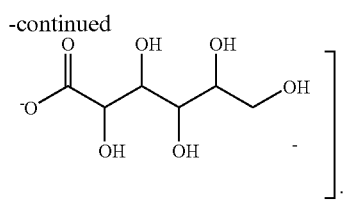

The trace metal derivatives of phosphorylated vitamin B derivatives, such as benfotiamine, for example Figure 9, and pyridoxal-5-phosphate, are highly useful for topical application. In a surprising and unexpected discovery, it has now been found that such topical applications of said derivatives provide enzyme-modulating effects on several other enzymes in addition to SOD. The enzymes thus modulated include superoxide Dismutase (SOD), matrix metalloproteases (MMP) and Advanced Glycation End Products (AGES). The modulation of such enzyme functions now provides topical skin care benefits such as antiaging, skin whitening, acne control, skin condition improvement, collagen promotion, wrinkles reduction, hair growth modulation, and intra-cellular antioxidant via a single trace metals delivery system of the present invention. The present invention also discloses a method for topical penetration of trace metals; and comprises (i) mixing of a trace metal salt of a phosphorylated nitrogen heterocyclic base complexed with a chelating agent, and (ii) a carrier, and (iii) topical application of said mixture. Glutathione and carnosine may also be included.

The present invention also discloses a topical composition comprising (i) a trace metal salt of a phosphorylated monosaccharide complexed with a chelating agent, and (ii) a carrier. These complexes are also useful for topical penetration of trace metals. These complexes do not contain a nitrogen heterocyclic base, thus they differ from a phosphorylated nitrogen heterocyclic base complexed with a chelating agent. The general features of these complexes are illustrated in [FIG. 10], wherein sodium metal ion can be replaced by trace metal ions, and such trace metal phosphorylated monosaccharide can then be complexed with a chelating agent. Alternatively, the trace metal salt of a chelating agent, for example, FIG. 11, can be combined with sodium phosphorylated monosaccharide to form phosphorylated-trace metal-chelating agent complex.

[FIG. 10]. Fructose-1,6,-Diphosphate, Sodium Salt.

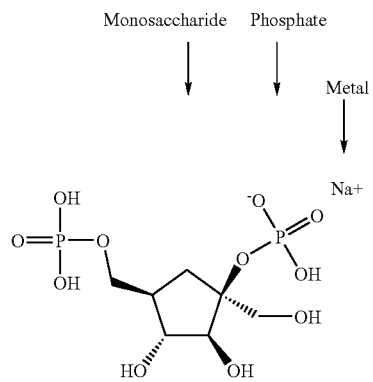

[FIG. 11]. Examples of Trace Metal Chelates.

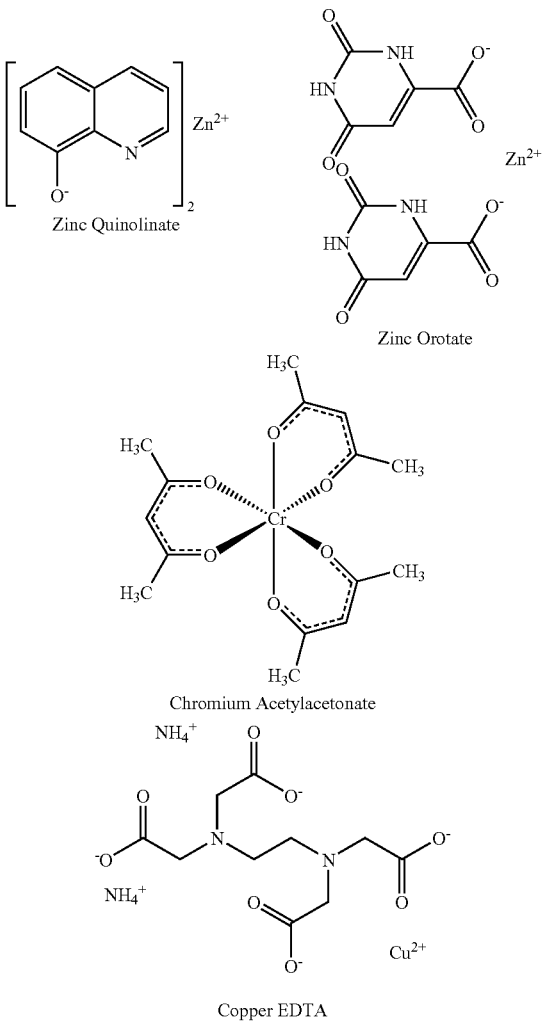

The examples of trace metal salt of a phosphorylated saccharide complexed with a chelating agent include copper, zinc, manganese, cobalt, chromium, selenium, or vanadium salt of fructose-1,6-diphosphate complexed with gluconic acid, citric acid, picolinic acid, EDTA, orotic acid, 8-hydroxyquinoline, an amino acid, a peptide, metal salts of said chelating agents, or combinations thereof. Glutathione and carnosine may also be included. Other phosphorylated mono or disaccharides can be used in place of fructose-1,6-diphosphate, for example, fructose 1-phosphate, fructose 6-phosphate, glucose 1-phosphate, glucose 6-phosphate, glucose diphosphate, mannose 1-phosphate, mannose 6-phosphate, and mannose diphosphate.

Benfotiamine is a derivative of thiamine (Vitamin B1). Benfotiamine (S-Benzoylthiamine-O-Monophosphate) is a member of the allithiamine group, a class of thiamin-derived compounds. Benfotiamine has an open-ring structure that makes it fat soluble and allows it to pass through cell membranes and be absorbed directly into cells. As such, it is the most potent of the allithiamines and makes it effective as a topical application as it can easily pass through the lipid bilayer of the cell membranes of epidermal and dermal cells. It has been used extensively in prior art in the treatment of diabetes. U.S. patent application Ser. No. 20050019354 A1

(Perricone) discloses certain topical applications of benfotiamine for skin condition improvement. Perricone has not disclosed any topical trace metal derivatives of benfotiamine, or Benfotiamine-Trace Metal-Chelating agent complex [for example, Figure 9].

Benfotiamine has been disclosed to alleviate diabetes related tissue damages, for example, Wu et al. (Neurosci. Lett, Oct. 27, 2005); and Haupt et al. (Int. J. Clint. Pharmacology Ther. 2005 February; 43 (2):71-7).

Trace metal salts of certain phosphorylated nitrogen heterocyclic bases are also known in the prior art. U.K. Patent Application GB 2,044,265A (Garay) discloses certain metal salts of adenosine triphosphate, and their application in the treatment of cerebrovascular and cerebrosclerotic diseases via ingestible compositions. Garay does not disclose the chemical structure of such trace metal salts of adenosine triphosphate. For example, Copper adenosine triphosphate can occur in two forms, as shown in [FIG. 12]. As has been discussed herein, the exact chemical nature of such copper derivatives can have profoundly different biological, chemical, and physical properties. Also, Garay does not disclose any Adenosine triphosphate-Trace Metal-Chelating agent complexes; or their topical application; or their use in the modulation of Superoxide Dismutase, or Elastase, or Tyrosinase, or Matrix metalloproteases, or Ubiquitin-Proteasome pathway enzyme systems. The present invention circumvents these difficulties as well.

[FIG. 12]. Cu-ATP Structures.

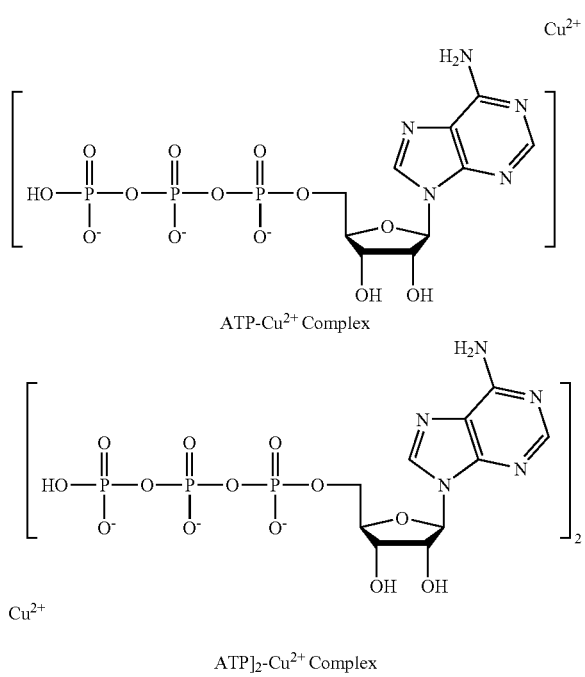

U.S. patent application Ser. No. 20030158171 (Ashmead et al.) discloses a method for reducing alcohol desire or dependency in a human can comprise the steps of administering a chelate or a combination of chelates to a human having alcohol dependency symptoms or an unwanted desire for alcohol. Ligands that can be used include carnitine, naturally occurring amino acids, and thiamine phosphate. Metals that can be used include nutritionally relevant metals, including copper, zinc, and manganese. Ashmead et al. thus do disclose certain trace metal salts of a phosphorylated nitrogen heterocyclic base, such as thiamine phosphate, but they do not disclose any Thiamine phosphate-Trace Metal-Chelating agent complexes; or their topical application; or their use in the modulation of Superoxide Dismutase, or Elastase, or Tyrosinase, or Matrix metalloproteases, or Ubiquitin-Proteasome pathway enzyme systems.

U.S. patent application Ser. No. 20060045896 (Morariu) discloses a composition comprising an effective amount of benfotiamine and an effective amount of pyridoxamine in a suitable vehicle for topical application, which are useful in improving the appearance of aged skin characterized by wrinkles, loss of elasticity, and hyperpigmentation caused by chronoaging and/or photoaging of skin, by inhibiting particularly skin damage resulting from reactive carbonyl species (RCS), glycation of skin proteins, formation of advanced glycation endproducts (AGEs) and formation of advanced lipoxidation endproducts (ALEs). Morariu does not disclose any trace metal salts of a phosphorylated nitrogen heterocyclic base, such as benfotiamine, or any benfotiamine-trace metal-chelating agent complexes; or their topical application; or their use in the modulation of Superoxide Dismutase, or Elastase, or Tyrosinase, or Matrix metalloproteases, or Ubiquitin-Proteasome pathway enzyme systems.

U.S. patent application Ser. No. 20050019354 (Perricone) discloses certain topical compositions to improve skin condition comprise an effective amount of an allithiamine, such as benfotiamine, and a carrier. Methods for improving skin condition comprise applying a composition containing benfotiamine in a dermatologically acceptable carrier to skin tissue. Perricone teachings are very similar to those of Morariu. Perricone does not disclose any trace metal salts of benfotiamine, or any benfotiamine-trace metal-chelating agent complexes; or their topical application; or their use in the modulation of Superoxide Dismutase, or Elastase, or Tyrosinase, or Matrix metalloproteases, or Ubiquitin-Proteasome pathway enzyme systems.

DE 4110087 (Woerwag et al.) disclose certain benfotiamine topical compositions for the treatment of rheumatic disorders, general joint and muscle pains, root irritant syndrome of the spinal column, HWS-syndrome, shoulder-arm-syndrome, symptoms resulting from polyarthritis, tennis elbow, stiff neck, lumbago, sciatica, disc pain, arthroses, polyneuropathy, neuritis, migraines, neuralgia, shingles, facial paralysis. Benfotiamin is a lipid soluble analogue of vitamin B1. By applying it topically to the body parts affected, where it is then converted into thiamin or cocarboxylase, it is possible to achieve targeted local action. Woerwag et al. (EP 0820771) further disclose a combination of benfotiamine and magnesium orotate for the treatment of neuropathies. Woerwag et al. do not disclose any applications of benfotiamine for the transport of trace metals from their topical application.

DE 10353535 (Hartmann et al.) disclose a composition benfotiamine, a chromium salt, folic acid and optionally additives to form micropellets and introducing these into a hard gelatin capsule for oral dosage to provide antidiabetic, neuroprotective, and vasotropic benefits. Hartmann et al. do not disclose any applications of benfotiamine for the transport of trace metals from their topical application.

U.S. patent application Ser. No. 20060024367 (Byrd) discloses certain oral dosage formulation containing benfotiamine, a phosphorylated nitrogen heterocyclic base. Byrd does not disclose any benfotiamine, or any benfotiamine-Trace metal-chelating agent complexes; or their topical application; or their use in the modulation of Superoxide Dismutase, or Elastase, or Tyrosinase, or Matrix metalloproteases, or Ubiquitin-Proteasome pathway enzyme systems.

U.S. Pat. No. 5,443,834 (Aki et al.) discloses a topical soap composition with a garlic extract containing a phosphorylated nitrogen heterocyclic base, such as benfotiamine, thiamine pyrophosphate, dicethiamine, and cycotiamine. The soap is effective for improving atopic dermatitis. Aki et al. do not disclose any benfotiamine or thiamine pyrophosphate, or any benfotiamine-trace metal-chelating agent complexes, or thiamine pyrophosphate-trace metal-chelating agent complexes; or their topical application; or their use in the modulation of Superoxide Dismutase, or Elastase, or Tyrosinase, or Matrix metalloproteases, or Ubiquitin-Proteasome pathway enzyme systems.

U.S. Pat. No. 5,221,791 (Narayanan et al.) discloses certain amine derivatives of biologically active, acidic, organic compound selected from the group of a carboxylic, thiocarbonic, sulfonic, sulfinic, thiosulfonic, thioacid, mono- and di-thiophosphate and phosphorous containing acid, having a pKa value less than 5 negative logarithm, base 10, of the dissociation constant, Ka, such as benfotiamine. Narayanan et al. do not disclose any trace metal salts of benfotiamine or thiamine pyrophosphate, or any benfotiamine-trace metal-chelating agent complexes, or thiamine pyrophosphate-trace metal-chelating agent complexes; or their topical application; or their use in the modulation of Superoxide Dismutase, or Elastase, or Tyrosinase, or Matrix metalloproteases, or Ubiquitin-Proteasome pathway enzyme systems.

DEFINITIONS

The following terms used in the present invention have the meanings set forth below.

Amino Acid. Any of a group of organic compounds containing the amino group combined with the carboxyl radical.

Apoenzyme. Penultimate form of an enzyme that is not in its active form. A combination of apoenzyme with a cofactor, such as a trace metal, converts apoenzyme into a fully functional enzyme.

Base. A compound that is capable of so uniting with an acid as to neutralize it and form a salt.

Basic. A compound that has base-like or alkaline properties.

Bioinorganic. A compound of biomedical importance that has an inorganic moiety, such as a metal atom, in its basic structure. The basic structure of this molecule can be organic or inorganic.

Chelate. A chemical compound in the form of a heterocyclic ring, containing a metal ion attached by coordinate bonds to at least two nonmetal ions. Examples are shown in [Figure 11].

Dalton (Da). A Dalton (Da) is a unit of atomic weight, equal to 1/12 of the mass of a 12C atom. It is also referred to as an atomic mass unit (AMU). Most common usage is to describe molecular weights of biopolymers in units of kilo-Daltons (KDa). The average molecule weight of an amino acid is approximately 110 Da.

Derivative. A compound formed or regarded as being formed from a specified substance or another compound, usually by partial substitution.

Dialysis. Size of the pores is such that only small molecules (i.e. 3000 Da or less) can pass through them while proteins and other macromolecules cannot.

Dispersion. An emulsion or suspension. Comprise the dispersed substance and the medium it is dispersed in.

Emulsion. Intimate mixture of two incompletely miscible liquids.

Equimolar. Of equivalent molecular weight.

Hydrophilic. Strong affinity for water.

Hydrophobic. Weak affinity for water.

Inorganic. Pertaining to those compounds lacking carbon, but including carbonates and cyanides.

Ligand. A molecule that binds or forms a complex with another molecule. Usually considered to be a small organic molecule (e.g. glucose, ATP, etc.), but can range in characteristics from metal ions (e.g. Ca2+) to a protein (e.g. lysozyme can be considered the 'ligand' when it forms a complex with an anti-lysozyme antibody).

Lipophilic. Strong affinity for fats or other lipids.

Low Molecular Weight (LMW). The molecules of size 3000 Da or less that can pass through a dialysis membrane. For the purpose of present invention, the molecule size of LMW is less than 1000 Dalton units.

Metal Complex. A metal complex, also known as coordination compound, is a structure composed of a central metal atom or ion, generally a cation surrounded by a number of negatively charged ions or neutral molecules possessing lone pairs of electrons. Counter ions often surround the metal complex ion, causing the compound to have no net charge. The ions or molecules surrounding the metal are called ligands. Ligands are generally bound to a metal ion by a coordinate covalent bond, and are thus said to be coordinated with the ion. The process of binding to the metal ion with greater than one coordination site per ligand is called chelation.

Miscible. Capable of mixing in any ratio without separation of the two phases. The mixture formed by a miscible liquid or solid is a solution.

Modulation. Adjusting, or regulating in proper measure or proportion.

Molecular Weight. Total weight of a molecule, usually given in Daltons (Da) or kilo-Daltons (kDa).

Nitrogen Heterocyclic Base. Heterocyclic compounds are organic compounds that contain a ring structure containing atoms in addition to carbon, such as nitrogen, as part of the ring. Nitrogen heterocyclic bases, or sometimes referred to as nitrogenous bases, are nitrogen heterocyclic compounds, for example purines, pyrimidines, nucleosides, and nucleotides.

Nucleoside. On of the nitrogen heterocyclic bases bonded to a sugar molecule makes a nucleoside. For example, when the heterocyclic base adenine bonds with the sugar molecule ribose by an intermolecular dehydration the nucleoside adenosine is formed.

Nucleotide. Nucleoside with one or more phosphate groups attached to the sugar moiety of nucleoside forms a nucleotide. For example, adenosine combines with the phosphate (or phosphoric acid) to form the nucleotide adenosine monophosphate. It is quite often abbreviated as AMP. It can also be called adenylic acid.

Oleophilic. Strong affinity for oils.

Organic. Being, containing, or relating to carbon compounds, especially in which hydrogen is attached to carbon whether derived from living organisms or not.

Organic solvent. A solvent including a carbon compound. Examples include, without limitation, glycerin, PEG-6 (Polyethylene glycol 300), and Methylpropanediol (MP glycol).

Parts per Million (ppm). The number of parts of a material or molecule in one million parts of a composition. For example, if 1% copper gluconate is added to a composition, then that composition contains 10,000 parts of copper gluconate (or, 1400 ppm of copper ions, since copper gluconate contains 14% copper in it) in one million parts of that composition.

Phosphorylated. Made by the reaction of phosphoric acid or its precursor, such as phosphorus pentoxide or phosphorous trioxide, with a hydroxyl group to form an acid ester. Also, introduction of a phosphate group into an organic molecule. Phosphorylation is the addition of a phosphate (PO4) group to a protein or a small molecule.

Phosphorylated Nitrogen Heterocyclic Base. Nitrogen heterocyclic bases, or sometimes referred to as nitrogenous bases, that are attached to an alkanol or simple sugar moiety to which at least one phosphate group is also attached. The examples are various nucleotides, benfotiamine, and Thiamine diphosphate.

Saccharide. An essential structural component of living cells and source of energy for animals; includes simple sugars with small molecules as well as macromolecular substances; are classified according to the number of monosaccharide groups they contain. Also, any of a series of compounds of carbon, hydrogen, and oxygen in which the atoms of the latter two elements are in the ratio of 2:1.

Signs of Skin Aging. These include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles and coarse deep wrinkles, skin lines, crevices, bumps, large pores (e.g., associated with adrenal structures such as sweat gland ducts, sebaceous glands, or hair follicles), or unevenness or roughness, loss of skin elasticity (loss and/or inactivation of functional skin elastin), sagging (including loss and/or damage to functional subcutaneous muscle tissue and including puffiness in the eye area and jowls), loss of skin firmness, loss of skin tightness, loss of skin recoil from deformation, discoloration (including under eye circles), blotching, shallowness, hyper pigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

Small Molecular Weight (SMW). The molecules of size 3000 Da or less that can pass through a dialysis membrane. For the purpose of present invention, the molecule size of SMW is less than 1000 Da.

Solution. A solid, liquid, or gas mixed homogeneously with a liquid.

Solvent. A substance capable of, or used in dissolving or dispersing one or more other substances, especially a liquid component of a solution present in greater amount than the solute. The examples include water, alcohol, glycol, propylene glycol, butylene glycol, pentylene glycol, hexylene glycol, polyethylene glycol, polypropylene glycol, methylpropanediol, ethoxydiglycol, glycerin, diglycerol, polyglycerol, and combinations thereof.

Suspension. Particles mixed in a fluid or a solid, but undissolved.

Synergism. The joint action of different substances in producing an effect greater than the sum of effects of all the substances acting separately.

Synergistic. Acting together.

Trace Metal. Any of certain chemical metallic elements found in very small amounts in plant and animal tissues and having a significant effect upon biochemical processes.

Water miscible organic solvent. An organic solvent that can be mixed with water in any ratio without separation of the water from the organic solvent. In the practice of the invention, the preferred (but not required) water miscible organic solvents are those commonly used in cosmetic applications, for example, glycerin, ethylene glycol, propylene glycol, butylene glycol, hexylene glycol, pyrrolidone, N-methyl pyrrolidone, dimethyl sulfoxide, dimethyl sulfone, polyethylene glycol, polypropylene glycol, methylpropanediol, and similar solvents.

EXAMPLES

The following examples are for illustration purposes only, and they do not represent any limitation or scope of the present invention. All compositions are in weight percentages. The color measurements were done on a Hunter Lab color meter. This color meter measures color on a scale defined as L, a, b scale. "L" is a valve from 100 to 0, representing white and black colors (lightness and darkness). L=100 shows indicates white color. L=0 indicates pure black color. A (−) value of "a" indicates green color. A (+) value of "a" indicates red color. A (−) value of "b" indicates blue color. A (+) value of "b" indicates yellow color. Various numeric values of "a" and "b" indicate the degree of respective colors. The mixed colors are thus indicated by a mixed value of "L, a, b" as will be noted in various examples below. The materials used had the following properties. Adenosine triphosphate disodium hydrate (molecular weight 551 Da), glutathione (molecular weight 307 Da), copper gluconate (molecular weight 453 Da, Cu=14%), copper amino acid chelate (copper 12%), fructose-1,6-diphosphate dicalcium (molecular weight 416 Da), zinc gluconate (molecular weight 455 Da, Zn=14%), manganese gluconate (molecular weight 445 Da, Mn=12%).

Example 1

The Process for Copper Benfotiamine Gluconate [(Benfotiamine) (Cu) (Gluconate)] Complex. Ingredients. Part "A". (1) Copper Gluconate 2.25 (2) Deionized Water 97.75. Part "B". (1) Benfotiamine Sodium 2.75 (2) Deionized Water 97.25. Procedure: Mix ingredients of Part "A" in a beaker. A clear blue solution was obtained. It had a pH of 4.0, and the color readings were L=36.15, a=−42.07, b=−6.55. These data indicate that "a" had a (−) value (green), and "b" also had a (−) value (blue). This means the solution was greenish blue in color. This was identified as solution, Part "A". Ingredients of Part "B" were mixed in a separate beaker. A clear, water-like solution was obtained. It had a pH of 3.1, and the color readings were L=68.32, a=−0.82, b=+0.23. Since both "a" and "b" are negligible numbers (less than 1), that indicates that the sample had no color in it. This was identified as solution Part "B". Solutions of Part "A" and Part "B" were then mixed. A color change was immediately noted. The solution still remained clear, and no precipitate or discoloration noted. This solution was identified as solution of "Cu-Benfotiamine-Gluconate", which was identified as "C", and had a pH of 4.0, and the color readings were L=53.52, a=−33.58, b=−4.19. It had a copper concentration of 1575 parts per million (ppm), or 0.1575%. Since "C" obtained above had only half the amount of total copper, compared to solution Part "A", a fresh solution of copper gluconate was obtained that contained only half the amount of total copper compared to solution Part "A", but it still had the same amount of total copper as the solution of "C" obtained above. This fresh solution of copper gluconate was obtained by mixing 1.13 grams of copper gluconate in 98.87 grams of deionized water. The light blue clear solution thus obtained had a pH of 4.1, and the color readings were L=48.26, a=−34.28, b=−7.76. It was identified as solution "D". A comparison of solution "C" and "D" made above shows that the "b" color reading of solution "C" had become less negative (i.e. "C"

had shifted to a lesser blue color, shifting the color to a greenish blue) than that of solution "D. This clearly confirms that copper had coordinated with benfotiamine to form Cu-Benfotiamine-Gluconate complex in "C". Same color change (i.e. turning to a more greenish blue color for sample "C") was observed visually, as mentioned above. This confirms that the "Lab" color readings were correlatable to visual observations. However, the "Lab" color readings are more quantitative and measurable for exact comparisons, as these data can also be obtained via a spectroscope at varying wavelengths and plotted as shown in [FIG. 13]. For this reason, the stability of Cu-Benfotiamine-Gluconate solution was also measures by this method, as described in Example 2.

Example 2

The Stability of Cu-Benfotiamine-Gluconate from Example 1

The solution "C" obtained per Example 1 was stored in a beaker with a plastic film wrapped over it. It was stored in full light (fluorescent lamps) under ambient room temperature conditions. The color readings were measured periodically, and any visually observed discolorations, or precipitate formations, if any, were also recorded. Initial (1 Week) [4 Weeks]; "L" 53.52 (51.35) [51.54]; "a"-33.58 (−35.38) [−36.08]; "b"-4.19 (−5.16) [−5.56].

Example 3

Process for Cu-Benfotiamine-Glutathione [(Benfotiamine) (Cu) (Glutathione)] Complex Ingredients. Part "A". (1) Copper Gluconate 2.25 (2) Deionized Water 47.75. Part "B". (1) Benfotiamine Sodium 2.75 (2) Deionized Water 47.25. Part "C". (1) Glutathione 1.50 (2) Deionized Water 48.5. Procedure: Mix all "Part A" ingredients. A clear blue solution is obtained. Mix all "Part B" ingredients in a separate container. A clear, water white solution is obtained. Mix all "Part C" ingredients in a separate container. A clear water white solution is obtained. Mix solution of "Part A" with solution of "Part B". A greenish blue solution is obtained, as in Experiment 1. Add solution of "Part C" to above mixture of solution "Part A" and "Part B". A bluish green precipitate was immediately formed. The analysis of this precipitate shows that both glutathione and copper to be present. Cu content was 2100 ppm. This shows instant binding of Copper with Benfotiamine and Glutathione to form the new complex in-situ.

Example 4

Calculation of Parts Per Million of Copper in a [Copper-Benfotiamine-Chelating Agent] Complex. First, the parts per million (ppm) of copper content of a copper donor is calculated by; Cu ppm in Cu Donor=(% Cu in Cu Donor×10,000)/100. Then, Cu donor (%) needed in a composition to meet a required ppm of Cu is calculated by; % Cu donor needed=(1/Cu ppm in donor)×Cu ppm desired. For example, a Cu donor, such as Copper amino acid chelate that has a Cu content of 20%, has the following ppm content; Cu ppm in Cu amino acid=(20×10,000)/100=2000 ppm. To obtain a 150 ppm level of Cu in a composition, the following % of Cu amino acid chelate will be needed; % Cu amino acid needed=(1/Cu ppm in Cu amino acid)×ppm desired; % Cu amino acid needed= (1/2000)×150=0.075%. The following formula can be used for this calculation; ((63/mol.wt. of Cu source×wt. of Cu source)/total weight of composition)×1000000; in which, 63 is the atomic weight of copper, "mol.wt. of Cu source" is the molecular weight of copper "donor", "wt. of Cu source" is the weight of copper "donor" used, "total weight of composition" is the total weight including all other additives, etc. in a composition. To illustrate, in Example 1, molecular weight of copper gluconate is 453. If 2.25 grams of copper gluconate was used to make a 200-gram composition, identified as "C". The copper content of "C" is; ((63/453×2.25)/200)× 1000000=1564 ppm, or 0.1564%.

Example 5

Calculation of % Amount of Copper Chelate Needed for a Specific Parts per Million Copper Content in a Process for [Nitrogen heterocyclic Base-Trace Metal-Chelating Agent] Complex. Use the following formula, (1/ppm of Cu source)× ppm Cu desired=% Cu source needed. For example, a Cu donor, such as copper amino acid chelate with a Cu content of 20%, has 2000 ppm Cu content, as calculated above. To have 100 ppm of Cu in a lotion or cream product, for example, copper amino acid required is, (1/2000)×100=0.05%.

Example 6

Process for a [Copper-Benfotiamine-Gluconate] Complex in a SOD Activating Serum Carrier with Zinc and Manganese as Cofactor Trace Metals. Ingredients. (i) Deionized Water to 100.00 (ii) Aristoflex AVC 1.0 (iii) Geogard-221 0.5 (iv) PEG-6 20.0 (v) Zinc Gluconate 0.01 (vi) Copper Gluconate 0.025 (vii) Manganese Gluconate 0.0001 (viii) Benfotiamine 0.2 (ix) Glutathione 0.1 (x) Fragrance 0.15 (xi) Botanical Extracts blend 0.25 (xii) Silicone Elastomer 5.0. Procedure: All copper donors (copper gluconate, zinc gluconate, and manganese gluconate) were mixed in water to give a greenish blue solution. To this solution, Benfotiamine and glutathione were added with mixing. A clear, purplish blue solution was obtained, which indicated a color shift and the transfer of copper from its donors to Benfotiamine. Aristoflex AVC was then added to it and the mixture mixed for 30 minutes to form a clear greenish blue gel. All other ingredients were then added to it with mixing. A purplish blue gel was obtained. The product had Zn=14 ppm, Cu=35 ppm, and Mn=0.12 ppm.

Example 7

A Method for Topical Penetration of Cu, Zn, and Mn Trace Metals in a Skin Lotion Carrier. (A) A nitrogen heterocyclic base-trace metal-chelating agent complex of the following process is first obtained; (1) Water to 100.00 (2) Mineral Oil 1.0000 (3) Phenoxyethanol 0.9000 (4) Glycerin 3.8000 (4) Deodorized Jojoba Oil 0.0001 (5) Vitamin E Acetate 0.0001 (6) Aloe Vera 0.0001 (6) Panthenol 0.0001 (7) Methyl Paraben 0.2000 (8) Propyl Paraben 0.1000 (9) PGMS-SE 2.0000 (10) Stearic Acid 3.0000 (11) Cetyl Alcohol 1.2000 (12) Caustic Soda 0.0001 (13) Deionized Water 1.0 (14) Manganese Gluconate 0.001 (15) Copper Amino Acid Chelate 0.025 (16) Zinc Gluconate 0.01 (17) Benfotiamine Sodium 0.2 (18) Glutathione 0.1 (19) Fragrance 0.6 (20) Botanical Extract 0.65. Procedure: All copper donors were dissolved in water to give a clear greenish blue solution. Benfotiamine and glutathione were then added to it. The color changed to purplish blue. This solution was then added to "skin lotion base" with mixing, and all remaining ingredients were also added. A sky blue lotion was obtained. Skin lotion base was obtained by mixing all other ingredients together, then heating at 70 to 80 C for one hour, and then cooling to ambient temperature with mixing. A white lotion was obtained which contained Cu=30 ppm, Zn=14 ppm, and Mn=1.2 ppm. (B) The nitrogen heterocyclic base-trace metal-chelating agent complex in the skin lotion base thus processed is applied to appropriate skin surface and allowed to penetrate. (C) An analysis of stratum corneum samples taken periodically via well-known tape stripping method showed that the penetration was rapid and complete within one hour.

Example 8

The Process for Night Cream Carrier with Copper Pyridoxal-5-Phosphate Amino Acid [(Pyridoxal-5-phosphate)(Cu)(Amino Acid)] Complex and Method of Its Application for an Anti-Aging Topical Treatment. (A) A nitrogen heterocyclic base-trace metal-chelating agent complex of the following process is first obtained; (1) Water to 100.00 (2) Carbomer 0.2 (3) GMS-SE 2.0 (4) Stearic Acid 3.0 (5) Cetyl Alcohol 1.5 (6) Glycerin 1.0 (7) Jojoba Oil 0.1 (8) Sweet Almond Oil 0.2 (9) Sesame Oil 0.2 (10) Apricot Kernel Oil 0.2 (11) Panthenol 0.0001 (12) Glydant Plus (Preservative) 0.2 (13) Dimethicone 2.0 (14) Vitamin E Acetate 0.0001 (15) Vitamin A Palmitate 0.0001 (16) Copper Amino Acid Chelate 0.025 (17) Pyridoxal-5-Phosphate 0.1 (18) Glutathione 0.05 (19) Fragrance 0.15 (20) Botanical Extract 0.25. Procedure: Copper amino acid chelate and Pyridoxal-5-Phosphate were dissolved in part of water (5% water). Glutathione were then added to it and the mixture stirred. It formed a precipitate of copper-Pyridoxal-5-Phosphate-Amino Acid-glutathione complex. All other ingredients except fragrance and botanical extract were mixed separately and heated at 70 to 80 C, then cooled to room temperature. The trace metal complex pre-blend made above, fragrance, and botanical blends were all added to the main batch and the batch mixed. A light blue cream was obtained with copper content of 30 ppm. (B) The complex thus obtained in the night cream carrier is applied to facial skin. (C) After repeated applications, once a day for four weeks, significant reduction of facial wrinkles and increased suppleness of skin were noted.

Example 9

Process for [Copper Pyridoxal-5-Phosphate Gluconate] Complex in a Face & Body Cleanser Carrier with Different Donor Sources of Copper. (1) Water to 100.00 (2) Germall-II 0.1 (3) Kathon CG 0.06 (4) Sodium Lauryl Sulfate 18.0 (5) Cocamidopropyl betaine 10.0 (6) Citric Acid 0.15 (7) Copper Gluconate 0.025 (8) Copper Amino Acid Chelate 0.025 (9) Pyridoxal-5-Phosphate 0.2 (10) Fragrance 0.5 (11) Botanical Extracts 0.2. Procedure: All copper donors were dissolved in part of water (5% water) from the batch. Pyridoxal-5-Phosphate was then added to it with mixing to form the pre-blend. All remaining ingredients were then mixed in a separate tank. The pre-blend was then added to the main batch with mixing. A greenish blue syrupy cleanser product was obtained that contained 65 ppm of Cu.

Example 10

Process for [Benfotiamine-Trace Metals-Gluconate] Complex in a Cosmetic Gel Carrier. Ingredients. (1) Deionized Water to 100.00 (2) Xanthan Gum 1.5 (3) Glutathione 0.15 (4) Aloe Vera powder 0.2 (5) Dehydroacetic acid (and) benzyl alcohol 0.5 (6) Sodium Hyaluronate 0.1 (7) Silicone Elastomer 4.0 (8) Polysorbate-20 6.0 (9) Copper Gluconate 0.23 (10) Zinc Gluconate 0.23 (11) Benfotiamine 0.55 (12) Deionized Water 5.0 (13) Glycerin 40.0 (14) Fragrance 0.2. Procedure: Mix deionized water and xanthan gum till hydrated. Mix copper gluconate, zinc gluconate, Benfotiamine, and deionized water (5.0% portion) to a clear, light blue solution. Add this solution to main batch and mix. Add all other ingredients and mix. A light blue clear gel is obtained with copper content of 322 ppm and zinc content of 322 ppm.

Example 11

Method for Topical Treatment of [Benfotiamine-Trace Metals-Gluconate] Complex in a Clear, High Potency Serum Carrier. (A) The following method is followed. (1) Ethoxydiglycol to 100 (2) Propylene Glycol 29.8 (3) Deionized Water 20.0 (4) Benfotiamine 3.51 (5) Pyridoxal-5-Phosphate 2.0 (6) Copper Gluconate 2.25 (7) Zinc Gluconate 1.1 (8) Manganese Gluconate 1.1 (9) Glutathione 0.3 (10) Deionized Water 5.0 (11) Grapefruit extract 0.1 (12) Fragrance 0.1. Procedure: Mix Benfotiamine, Pyridoxal-5-Phosphate, Copper gluconate, zinc gluconate, manganese gluconate, and deionized water (20% portion) till a clear greenish blue color is obtained (Premix A). Mix glutathione and deionized water (5.0 portion) in another container till a clear solution is obtained (Premix B). Mix ethoxydiglycol and glycerin in a main batch tank. Add all other ingredients and Premix A and Premix B solutions to main batch tank and mix. Filter this batch to remove any impurities. A greenish blue viscous solution is obtained that has copper content of 3150 ppm, zinc content of 1540 ppm, and manganese content of 1320 ppm. (B) This is used for topical penetration of Cu, Zn, and Mn in a high potency for eye zone and neck zone application and treatment. (C) This method of application accelerates SOD enzyme, which results in the removal of wrinkles and lightening of dark eye circles.

Example 12

Method for Eye Gel Carrier for Topical Application with [Copper Pyridoxal-5-Phosphate Gluconate] Complex and [Zinc Pyridoxal-5-Phosphate Gluconate] Complex in an Anhydrous Base. Ingredients. (1) Cyclomethicone 10.0 (2) Dimethicone 30.0 (3) Cyclomethicone (and) Dimethicone Crosspolymer-3 51.8 (4) Polysorbate-20 2.0 (5) Glutathione 0.1 (6) Zinc Gluconate 0.2 (7) Copper Gluconate 0.2 (8) Pyridoxal-5-Phosphate 0.2 (9) PEG-6 5.0 (10) Geogard-221 0.5. Procedure. All ingredients were mixed together till a bluish green suspension product was obtained. The topical application needs to be shaken before application to skin or hair. It had a copper content of 280 ppm and zinc content of 280 ppm.

What is claimed is:

1. A phosphorylated heterocyclic compound of formula (I) for topical application;

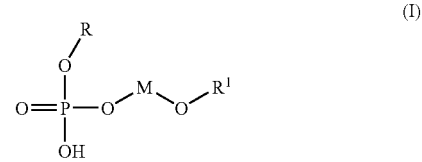

Wherein,

M is selected from Cu, Zn, Mn, Co, Cr, V=O, and Ni; and

R is selected from,

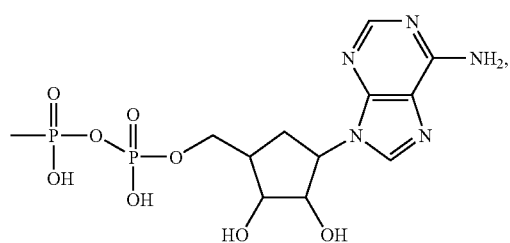
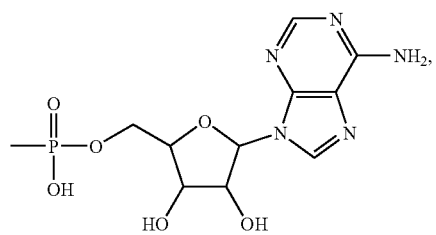
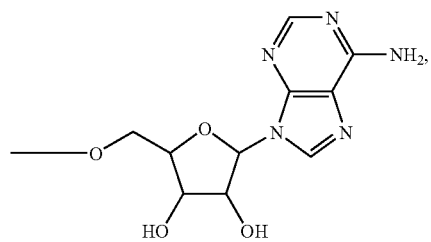
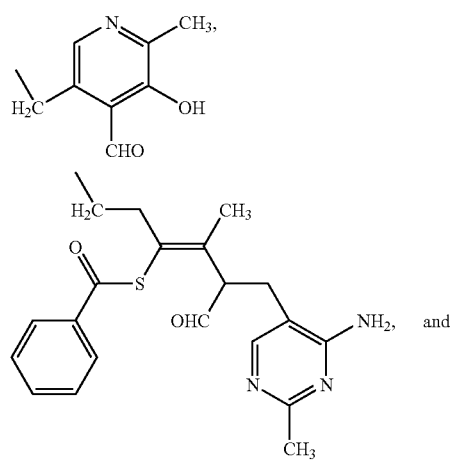
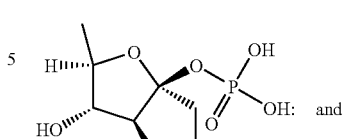
and
$R^1$ is selected from;
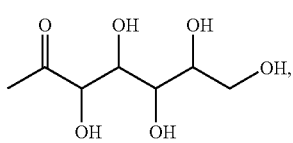
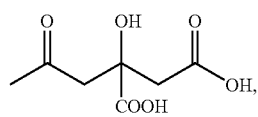
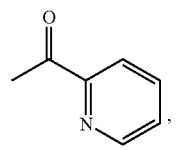
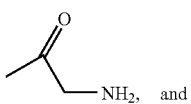
and
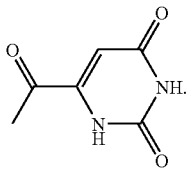
2. A composition comprising the compound of claim 1, for topical application.
3. A composition comprising the compound of claim 1, wherein said compound is copper adenosine triphosphate gluconate of formula (II);
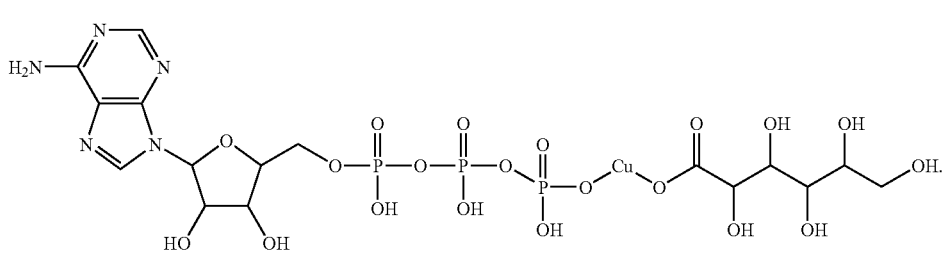

4. A composition comprising the compound of claim 1, wherein said compound is chromium benfotiamine picolinate of formula (III);

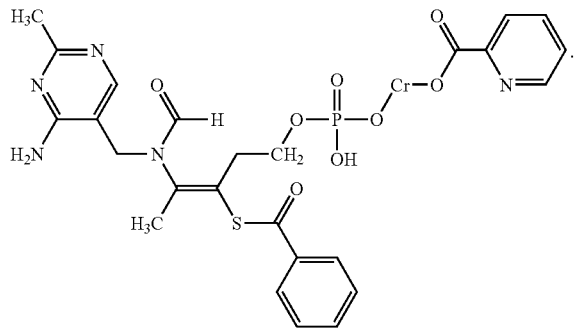

(III)

5. A composition comprising the compound of claim 1, wherein said compound is vanadium pyridoxal-5-phosphate oxo glycinate of formula (IV);

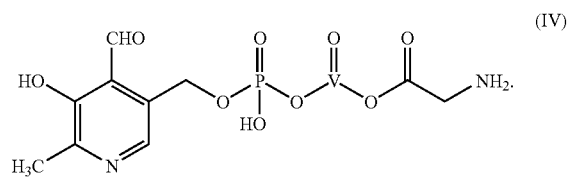

(IV)

6. A composition comprising the compound of claim 1, wherein said compound is from about 0.0001% to about 25% by weight of said composition.

7. The composition of claim 2 further comprising glutathione.

8. A method for topical delivery of trace metals comprising mixing of a trace metal phosphorylated heterocyclic compound of claim 1 with a carrier, and wherein said mixture is applied to skin.

9. The method of claim 8, wherein said mixture further comprising glutathione.

* * * * *